United States Patent [19]

Berke et al.

[11] Patent Number: 4,791,928

[45] Date of Patent: Dec. 20, 1988

[54] ROTARY SCALPEL METHOD

[76] Inventors: Joseph J. Berke, 3333 E. Jefferson, Detroit, Mich. 48207; George H. Muller, 2921 Overridge Dr., Ann Arbor, Mich. 48104

[21] Appl. No.: 422,847

[22] Filed: Sep. 24, 1982

[51] Int. Cl.⁴ .............................................. A61B 17/32
[52] U.S. Cl. ........................................ 128/305; 30/319
[58] Field of Search ................. 128/305, 1 R; 30/319, 30/292, 300, 306

[56] References Cited

U.S. PATENT DOCUMENTS

| 3,126,889 | 3/1964 | Blumenfeld ..................... 128/305 X |
| 4,111,206 | 9/1978 | Vishnevsky et al. ................. 128/305 |
| 4,140,123 | 2/1979 | Curvtchet ....................... 128/305 X |

FOREIGN PATENT DOCUMENTS 994256  11/1951  France ............................... 128/314

Primary Examiner—Michael H. Thaler
Attorney, Agent, or Firm—Dale R. Small & Associates

[57] ABSTRACT

A manual method of making a surgical incision in free tissue including moving a freely rotatable circular scalpel blade across an area of the free tissue at a desired incision depth without pressing the tissue to a mechanical backing member wherein the circular scalpel blade is rotated solely by friction between the blade and the tissue in which the incision is required. The scalpel blade may be pushed or pulled across the area of free tissue, preferably at a speed of between four and seven centimeters per second.

8 Claims, 5 Drawing Sheets

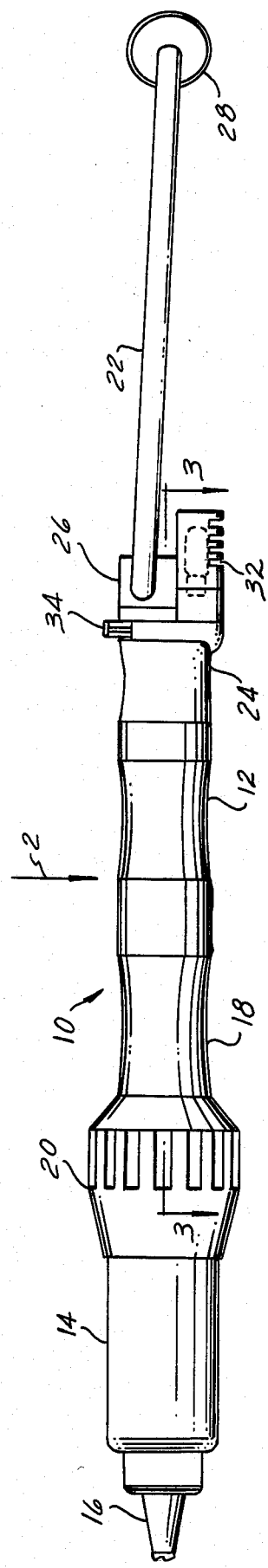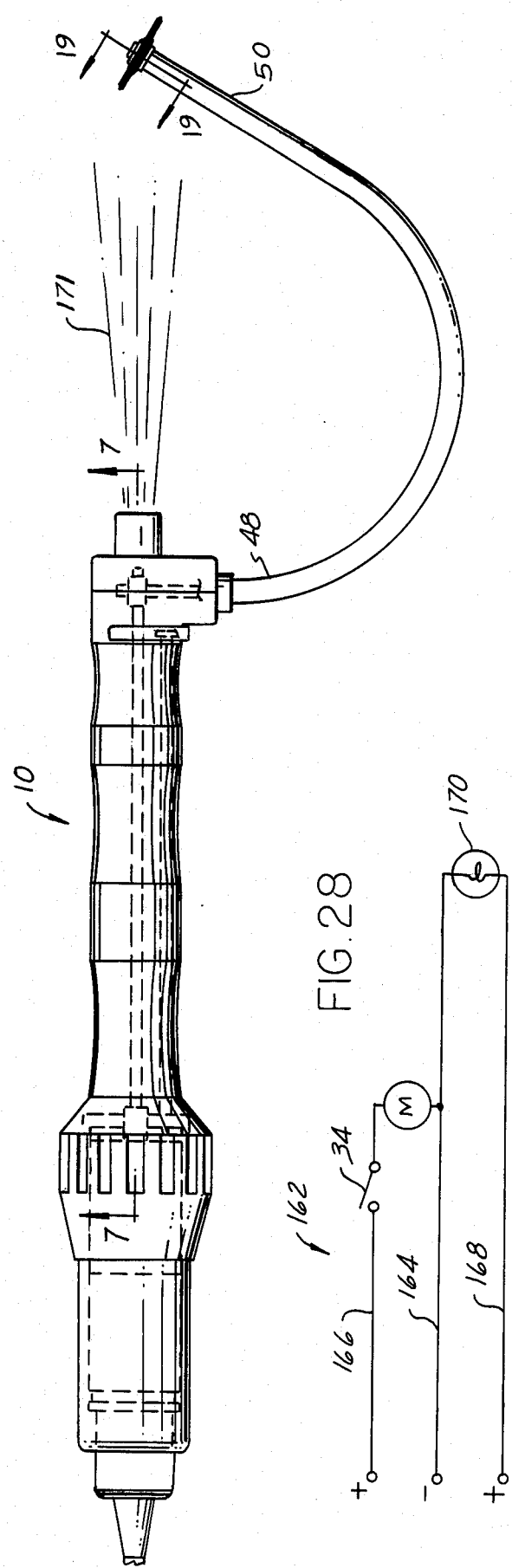

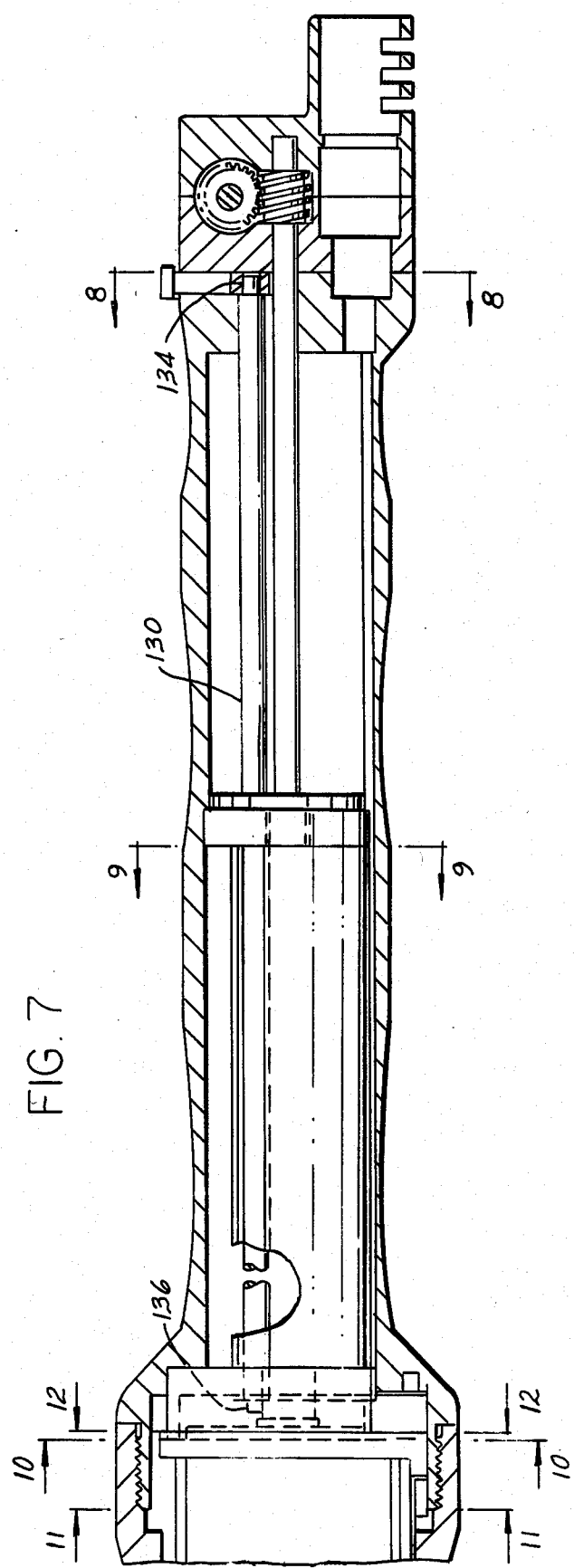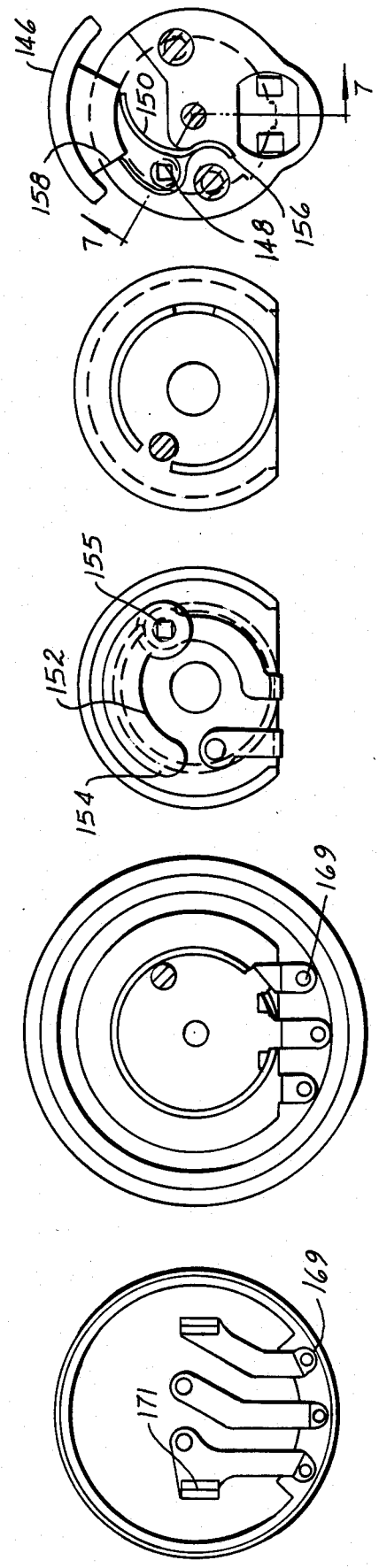

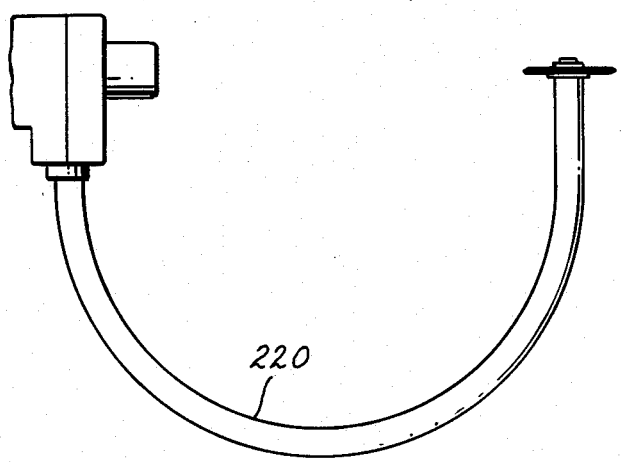
FIG. 22
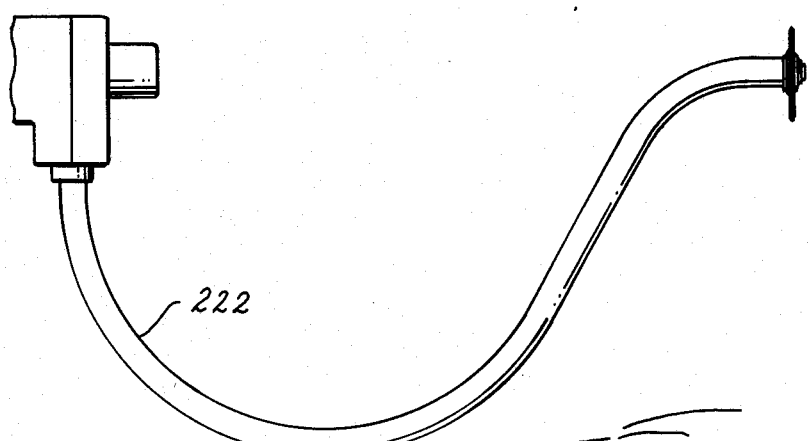
FIG. 23
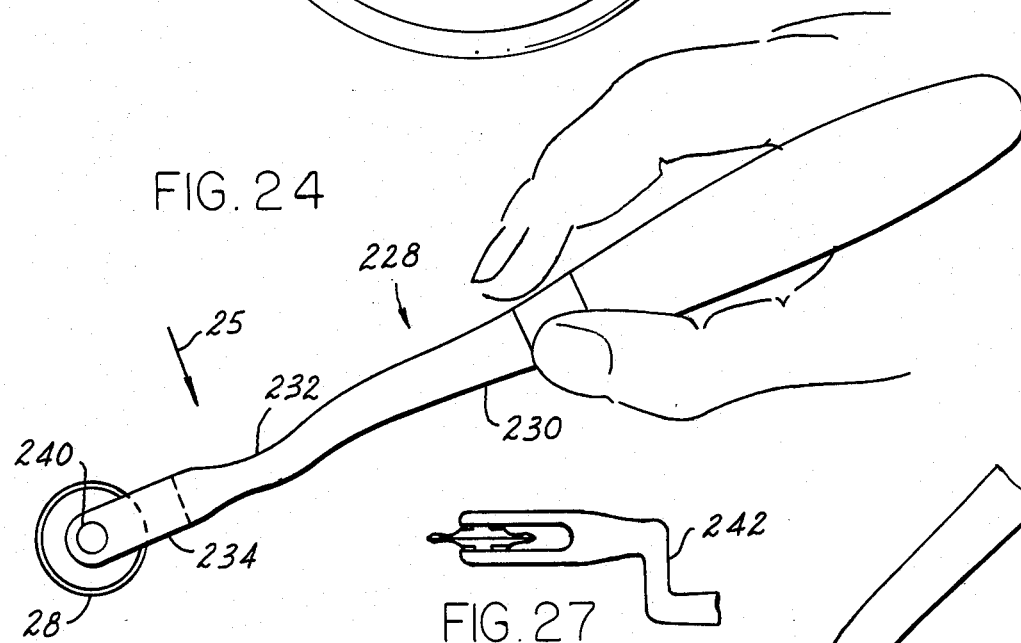
FIG. 24
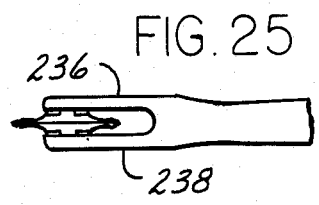
FIG. 25
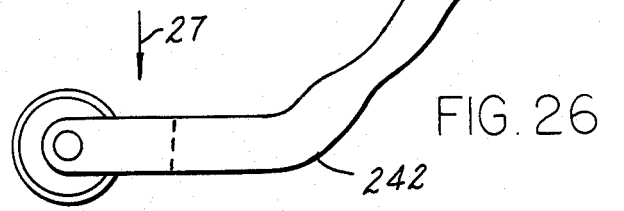
FIG. 27
FIG. 26

ROTARY SCALPEL METHOD

BACKGROUND OF THE INVENTION

1. Field of the Invention

The invention relates to surgery and refers more specifically to a rotary scalpel structure and method whereby an incision is made with a rotating circular scalpel blade having a circumferential speed preferably in the range of 4 to 7 centimeters per second so that scar tissue at an incision is minimized.

2. Description of the Prior Art

In the past, surgical incisions have generally been made with a straight scalpel used linearly which is essentially a straight sharp knife. With such structure, and particularly at the start of an incision, the material cut, i.e. human skin, is essentially crushed rather than cut as it would be by a moving blade as it is later during the making of the incision as the surgeon moves the blade across the area in which the incision is required. It is well known that with such scalpels and such procedures that in the crushed area, considerably more scar tissue will build up on healing of the incision than in the area where the scalpel is at the desired cutting depth and is moving along the incision plane while the incision is being made. Scar tissue is undesirable and should be minimized.

SUMMARY OF THE INVENTION

The rotary scalpel structure of the invention for practicing the method of the invention may be either a manual rotary scalpel or a automated, that is, power driven rotary scalpel.

The manual rotary scalpel may be straight or the rotary blade may be angularly off-set from the axis of the handle of the scalpel and the front end of the scalpel handle may be bifurcated so that the rotary scalpel blade may be rotatably mounted between the parts of the front end of the handle provided due to the bifurcation of the handle.

The power driven rotary scalpel includes a hollow cylindrical handle, a housing at one end of the handle for receiving an electric motor and electrical power for the rotary scalpel, a blade support arm at the other end of the handle on which a circular scalpel blade is mounted for rotation and means for driving the rotary scalpel blade through the support arm and handle from the motor including a gear box or boxes and support arm securing structure.

In accordance with the invention, the blade support arm is releasably secured to the handle by rotating pin structure, which pin structure may be bowed to reduce tolerance requirements.

The power driven rotary scalpel also includes a light for illuminating the area of the blade which is always on when power is applied to the power driven rotary scalpel to indicate a power on condition.

Remote switch structure is further provided for turning on the electric motor at the rear of the handle from the front of the handle.

The structure of the invention further includes a rotary scalpel blade having concave sides for reducing friction between the blade and tissue or other material being cut thereby and a hollow flat disc protector for rotary circular scalpel blades for user or manitenance protection including a living hinge and an axially split resilient cylinder closure therefore.

The method of the invention includes rotating a circular scalpel blade and drawing it across material in which an incision is desired. In the method of the invention, the rotary scalpel blade is rotated at a speed such that the circumferential speed of the rotary scalpel blade is between 4 and 7 centimeters per second which is the speed at which straight scalpels are moved in general practice.

BRIEF DESCRIPTION OF THE DRAWINGS

FIG. 1 is a side view of the power driven rotary scalpel constructed in accordance with the invention for performing the method of the invention.

FIG. 2 is a top view of the rotary scalpel illustrated in FIG. 1.

FIG. 7 is an enlarged, partial longitudinal section of the rotary scalpel shown in FIG. 1 taken substantially on the line 7—7 in FIG. 2.

FIG. 8 is a front end view of the handle of the rotary scalpel shown in FIG. 1 substantially on the line 8—8 in FIG. 7.

FIG. 9 is a front end view of the guiding and bearing member of the rotary scalpel shown in FIG. 1 substantially on the line 9—9 in FIG. 7.

FIG. 10 is a back end view of the guiding and bearing member of the rotary scalpel shown in FIG. 1 taken substantially on the line 10—10 in FIG. 7.

FIG. 11 is a back end view of the handle of the rotary scalpel shown in FIG. 1 taken substantially on the line 11—11 in FIG. 7.

FIG. 12 is a front end view of the motor housing of the rotary scalpel shown in FIG. 1 taken substantially on the line 12—12 in FIG. 1.

FIG. 22 is a top view of a modified scalpel blade support arm showing a circular scalpel blade mounted in parallel with and generally along the axis of the handle of the rotary scalpel of FIG. 1.

FIG. 23 is a top view of another modified scalpel blade support arm showing a circular scalpel blade mounted transversely of the axis of the handle of the rotary scalpel of FIG. 1 and generally rotating on or near the axis of the handle.

FIGS. 24 and 25 are an elevation view taken in the direction of arrow 25 and a partial top view of a manual embodiment of the rotary scalpel structure of the invention for practicing the method of the invention.

FIGS. 26 and 27 are a partial elevation view and a partial top view taken in the direction of arrow 27 of a modification of the manual rotary scalpel shown in FIG. 24 showing an off-set handle.

FIG. 28 is a schematic diagram of the electrical circuit of the rotary scalpel.

DESCRIPTION OF THE PREFERRED EMBODIMENTS

Figure 3:
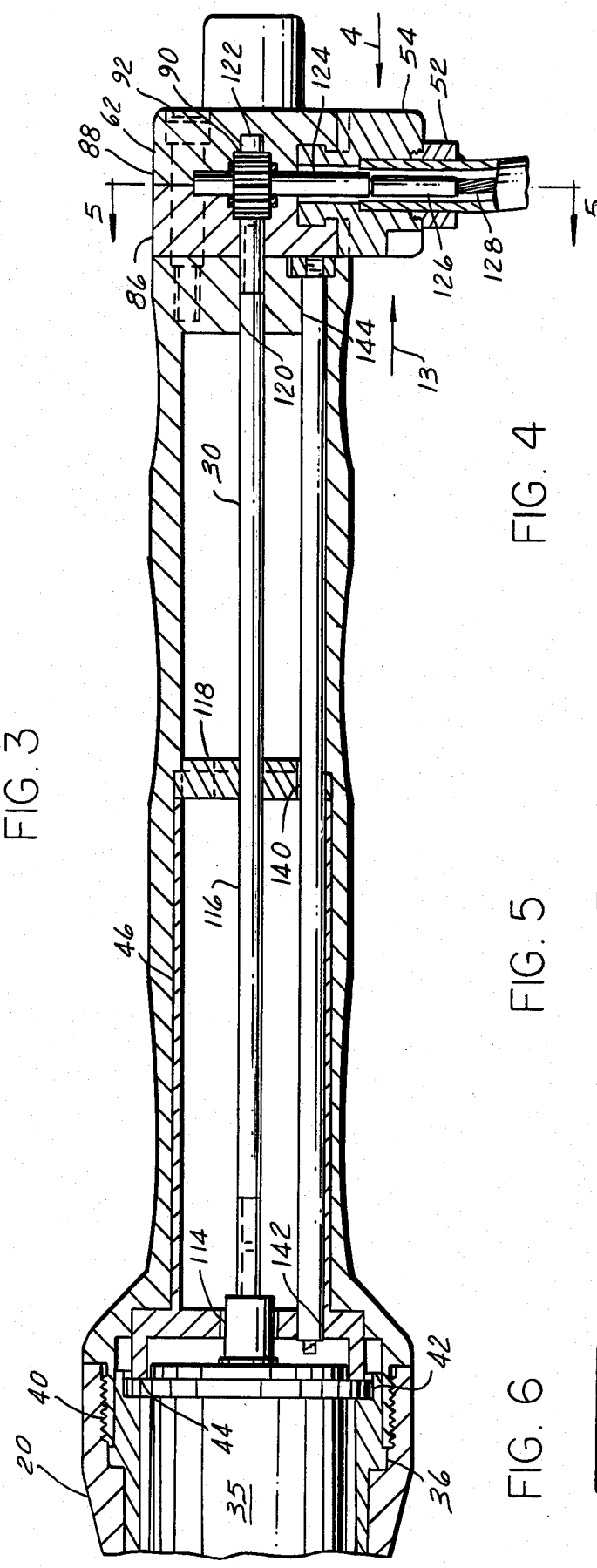
FIG. 3 is an enlarged, partial, longitudinal section view of the rotary scalpel shown in FIG. 1 taken substantially on the line 3—3 in FIG. 1.

The rotary scalpel structure 10 shown in FIGS. 1 and 2 and detailed in FIGS. 3 through 19, is a power driven or automatic rotary scalpel. The rotary scalpel structure 10 as shown includes a handle 12, motor housing 14 to which an electrical connector 16 is secured and which is secured to the back end 18 of the handle 12 by the coupling 20. A circular scalpel blade support arm 22 is connected to the front end 24 of the handle 12 through the securing structure 26 and gear box 62 and supports on its outer end the circular scalpel blade 28.

Structure 30 is provided extending through the handle 12 and blade support arm 22 for rotating the circular scalpel blade 28 on energization of the motor 30 in the housing 14. A light 32 is provided at the front end of the handle 24 to illuminate the scalpel blade 28. Remote switch structure 34 extends through the handle 12 to close a switch at the back end 18 of the handle 12 to energize the motor 30.

More specifically, the handle 12 as shown in FIGS. 1 and 2 has an exterior configuration adapted to facilitate gripping of the handle by a surgeon. The handle 12 is a hollow cylindrical member substantially closed at the front end having the longitudinal section configurations shown in FIGS. 3 and 7 and the end configurations shown in FIGS. 8 and 11.

The motor housing 14 as shown best in FIG. 3 is provided with a flange 36 thereon which is engaged by coupling 20 secured in a threaded connection 40 to the back end of handle 12 whereby the flange 42 on the motor 34 is held securely against the end 44 of the guiding and bearing member 46 of the remote switch structure 24.

The switch, guiding and bearing cylinder 46 which is cylindrical and shaped as shown in longitudinal section in FIG. 3, is positioned within the back end 18 of the handle 12 as will be considered in more detail and subsequently.

The electrical connector 16 provides a two wire electrical connection to the rotary scalpel structure 10. One of the incoming wires is a hot wire and may for example provide current at 4 amps from a variac at 6 volts while the second wire may be a grounded wire as will be considered subsequently in conjunction with the circuit of FIG. 27.

As shown best in FIGS. 1,2,3, and 19, the blade support arm 22 is a hollow tubular member, the back end 48 of which is secured at the front end 24 of the handle 12 and on the front end 50 of which the circular scalpel blade 28 is rotatably mounted. Member 52 permits securing the blade support arm 22 to the retaining structure 54 therefore in any desired angular position of the tubular blade support arm 22 or about its own axis.

Retaining structure 54 for securing the blade support arm 22 to the handle 12 through gear box 62 as illustrated best in FIGS. 13 through 16 includes a body member 56 shaped as shown to include an opening 58 therein for receiving the back end 48 of the blade support arm 22. The body member 56 further includes the annular flange 60 to prevent disengagement of the retaining structure 54 from the gear box 62 as will be considered subsequently and keys 62 to prevent rotation of the retaining structure 54 relative to the gear box 62.

Figure 13:
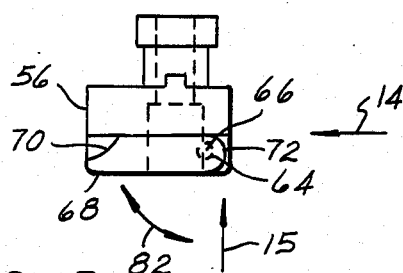
FIG. 13 is a back end view of the structure for securing the blade support arm to the handle of the rotary scalpel shown in FIG. 1 taken substantially in the direction of arrow 13 in FIG. 3.
Figure 14:
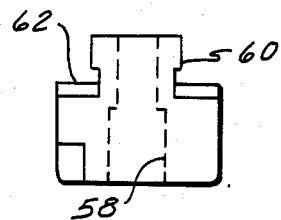
FIG. 14 is a top view of the structure illustrated in FIG. 13 taken in the direction of arrow 14 in FIG. 13.

Further, as shown best in FIG. 13, the retaining structure 54 is provided with a pin 64 extending through a passage 66 therein which is transverse of the opening 58 and extends thereinto radially. Pin 64 is rigidly secured to a lever 68 on the retaining structure 54 whereby on rotation of the lever 68 about the axis of the pin 64, the pin 64 is rotated about its own axis in the passage 66.

Figure 15:
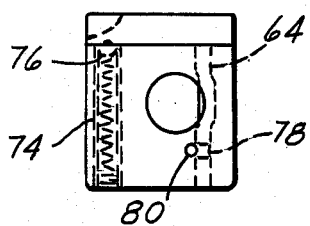
FIG. 15 is a side view of the structure illustrated in FIG. 13 taken in the direction of arrow 15 in FIG. 13.

Pin 64 is bowed slightly centrally along its longitudinal axis as shown in FIG. 15 to provide desired resistance to rotation about its own axis without additional parts and in tolerance requirements.

Rotation of the lever 68 about the axis of the pin 54 is facilitated by the recess 70 in the lever 68 and the rounded end 72 on the lever 68. Free rotation of the lever 68 is inhibited by spring pressed detent structure 74 and a depression 76 in the lever 68 as shown best in FIG. 15.

Pin 64 has an annular groove 78 extending therearound which is transversed by a further pin 80 extending through the body member 56 transversely of the pin 64 and into the annular groove 78. Thus, the pin 64 is allowed to rotate with the lever 68 but is prevented from being axially displaced from the body member 56.

Figure 16:
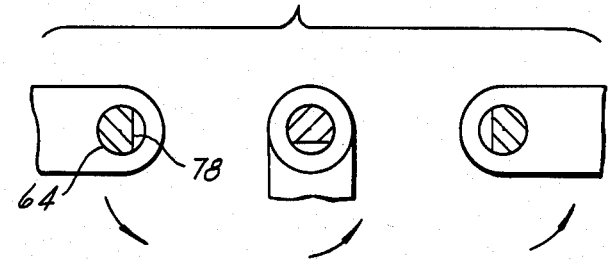
FIG. 16 is a composite figure showing three separate positions of the actuating member of the securing structure device shown in FIG. 13 progressively showing the pin secured thereto in a locking position and intermediate position and an unlocking position from left to right.

Further, as best shown in FIG. 16, the pin 64 is provided with a recess 78 in one side thereof which is so shaped that on rotation of the lever 68 into the position shown in FIG. 13, the recess 78 completely clears the opening 58 in the body member 56, that is to say, no part of the pin 64 appears in the opening 58. However, with such structure, with the lever 68 rotated 180° in the direction shown by the arrows 82 the pin extends into the opening 58.

Figure 5:
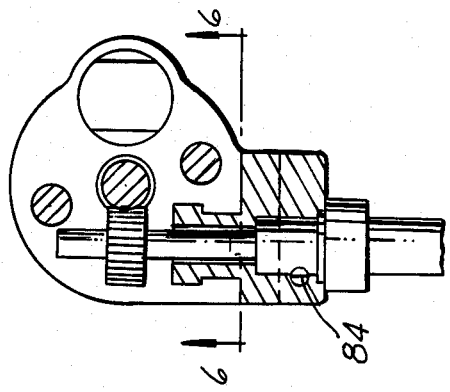
FIG. 5 is a cross section of the rotary scalpel shown in FIG. 1 taken substantially on the line 5—5 in FIG. 3.

Thus, referring specifically to FIG. 5, for example, the end 48 of the blade support arm 22 may be inserted in the opening 58, with the lever 68 positioned 180° from its location shown in FIG. 13 to rotate the pin 64 into the position shown in FIG. 16 at the right, wherein no portion of the pin 64 extends within the opening 58. The lever 68 is then rotated back into the position shown in FIG. 13 whereby the pin 64 is rotated into the position shown at the left in FIG. 16 through the intermediate position shown in the middle in FIG. 16 to provide a portion of the pin 64 positioned in the recess 84 in one side of the end 48 of the blade support arm 22. The blade support arm 22 is thus connected to the body member 56 of the retaining structure 54 against displacement axially of the end 48 of arm 22 thereof and against angular rotation relative to the body member 56.

Figure 4:
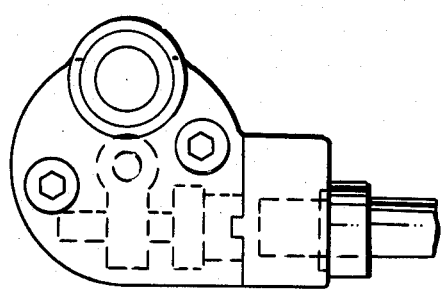
FIG. 4 is an end view of the portion of the rotary scalpel of FIG. 1 shown in FIG. 3 taken in the direction of arrow 4 in FIG. 3.
Figure 6:
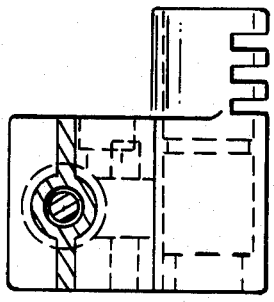
FIG. 6 is a cross section of the rotary scalpel shown in FIG. 1 taken substantially on the line 6—6 in FIG. 5.

As shown best in FIGS. 4, 5, and 6, the retaining structure 54 is held in place on the end 24 of the handle 12 by the gear box 62. The gear box 62 is split into two separate halves 86 and 88 positioned longitudinally of the axis of the handle 12 as shown best in FIG. 3. In assembly, the worm and worm gear structure 90 as shown best in FIGS. 3 and 5, is positioned in the gear box 62 along with the securing structure 54 and the gear box 62 is secured to the end 24 of the handle 12 by convenient means such as bolts 92. The light housing 32 is constructed integrally with the gear box 62 and supports an electric lamp 170 for illumination of the circular scalpel blade 28 as shown best in FIG. 1.

Figure 19:
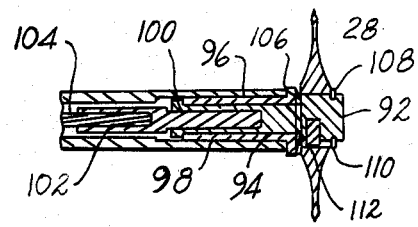
FIG. 19 is an enlarged section of the free end of the blade support arm and circular scalpel blade of the rotary scalpel structure illustrated in FIG. 1 taken substantially on the line 19—19 in FIG. 2 illustrating rotary mounting means for the scalpel blade illustrated in FIG. 17.

As shown best in FIG. 19, the circular scalpel blade 28 is mounted on the end 92 of a shaft 94 rotatably mounted in a pressed fit bearing 96 which is pressed into the end 50 of the blade support arm 22. Shaft 22 is connected by means of a non-circular axial opening therein 98 and a similar non-circular end 100 secured to the end 102 of flexible drive wire 104 extending through the blade support arm 22. Thus, in operation as the flexible drive wire 104 is rotated, the shaft 94 is rotated in the bearing 96 to rotate the circular scalpel blade 28.

Circular scalpel blade 28 is secured to the end 92 of the shaft 94 by abutment thereof against a dish shaped resilient washer 106 which urges the scalpel blade 28 outwardly of the shaft 94 and the resilient C-ring 108 positioned within the annular recess 110 around the end 92 of the shaft 94. Relative rotation between the shaft 92 and the circular scalpel blade 28 is prevented by means of the key 112 extending into both the circular scalpel blade 28 and the shaft 92.

Rotation of the flexible drive wire 104 is accomplished on energizing of the motor 34 to rotate the motor shaft 114. Rotation of the motor shaft 114 produces rotation of the shaft 116 extending through the guiding and bearing member 46 and the central bearing disc 118 assembled in the handle 12 as shown in FIG. 3 and the passage 120 through the end 24 of the handle 12. A right angle worm and worm gear drive are secured to the end 122 of the shaft 116 and the shaft 124 extending perpendicularly thereto in the gear box 62. Rotation of the shaft 30 through the worm and worm gear structure 90, thus causes rotation of the shaft 124. Shaft 124 again has an axially extending non-circular opening therein 126 into which a non-circular connector 128 of the flexible drive wire 104 extends. Flexible drive wire 104 is thus rotated on rotation of the shaft 124. Accordingly, when the motor 134 is energized, the circular scalpel blade 28 is rotated.

The remote switch structure 34 as shown best in FIGS. 3,7,8, and 10 includes a cylindrical shaft 130 having non-circular ends 134 and 136 which extends through the length of the handle 12 and through passage 140 in the bearing disc 118 passage 142 in the guiding and bearing member 46 of the switch structure and passage 144 in the end 24 of handle 12. Switch structure 34 further includes the actuating member 146 shaped as shown best in FIG. 8 having a non-circular opening 148 therethrough and the S-shaped spring 150. At the other end of the shaft 130, an electrical connector 152 is also connected by means of a non-circular opening 155 therethrough to the non-circular end 136 of the shaft 130. The end 156 of the spring 150 is rigidly secured in the end 24 of the body member 12.

Thus, in operation of the remote switch structure 24, the actuating member 46 is normally urged counterclockwise against the stop 158 formed in the end 24 of the handle 12. On pressing of the actuating member 146 it rotates about the axis of the shaft 130 with the shaft 130 against the bias of the spring 150 to produce rotation of the electrical connector 152 to close the circuit switch 34 shown in FIG. 27 to provide power to the motor 34.

On release of the actuating member 146, spring 150 returns the electrical connector 152 to its original position opening the circuit to the motor 34.

Thus, through the structure 34, electrical switching on and off of the motor 34 may be accomplished from the front end of the handle while the actual electrical switching takes place at the back end of the handle. This satisfies requirements for manual dexterity of the surgeon and removal of electrical switching from the material in which an incision is required.

Referring more specifically to the electrical circuit 162, shown in FIG. 28, it will be noted that the center conductor 164 is a ground line while conductors 166 and 168 are connected to a single hot or high voltage input spade, the line 164 and the line 168, go directly to the lamp 170 whereby when the electrical connector 16 is attached to the circular scalpel 10, the lamp 170 is always lit providing illumination from the light structure 32. The remote switch structure 34, shown schematically in FIG. 27, then opens and closes the conductors to the motor 35 through the hot line 166 and the ground 164.

The conductors 164,166 and 168 as shown best in FIGS. 8 through 12, are essentially strap conductors which make sliding contact with each other between the body member 12, the guiding and bearing member 46. Bayonet connectors 169 are provided between the housing 14 and the guiding and bearing member 46, while electrical spade connectors 171 are provided between the electrical connector 16 and the housing 14. Thus, easily manufactured positive electrical connections are provided throughout the circular scalpel structure 10 of the invention.

Figure 17:
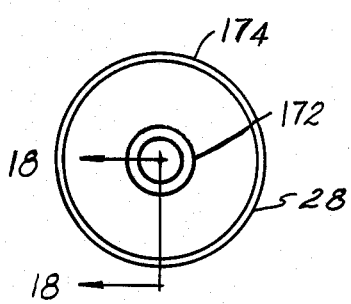
FIG. 17 is a side view of a circular scalpel blade constructed in accordance with the invention.

Referring more specifically to FIG. 17, the circular scalpel blade 28 is a substantially flat disc having the opening 172 extending axially through the middle thereof and having the outer periphery 174 sharpened. Both sides 176 and 178 of the circular scalpel blade 28 are concave as shown best in FIG. 18, whereby friction of material being cut against the scalpel blade 28 is materially reduced during use of the rotary scalpel structure 10.

In operation of the circular scalpel structure 10, for best results in minimizing formation of scar tissue at the start and indeed all along an incision, it has been found that driving the rotary scalpel blade 28 at a peripheral speed of between 4 and 7 centimeters per second is particularly desirable. Thus, the speed of the motor 34, the gear reduction in the motor and of the worm and worm gear structure 90 and the diameter of the circular scalpel 28 have been chosen to provide such a peripheral speed. Other peripheral speeds may of course be provided when considered suitable for specific surgical conditions.

Figure 21:
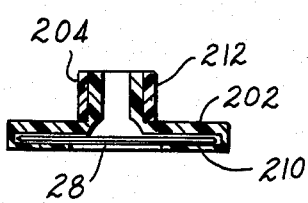
FIG. 21 is a cross section of the blade retainer structure illustrated in FIG. 20 taken substantially on the line 21—21 in FIG. 20.
Figure 20:
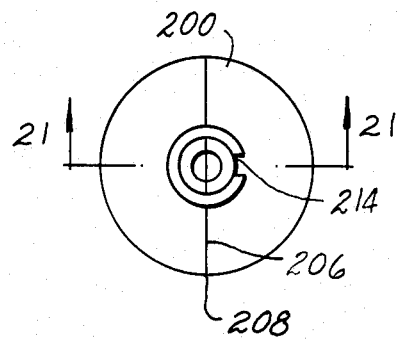
FIG. 20 is a top view of blade protector structure constructed in accordance with the invention for the scalpel blade illustrated in FIG. 17.

The blade protector structure 200 shown in FIGS. 20 and 21, includes a flat hollow disc 202 having a stem 204, which is also hollow extending from one side thereof. The discand stem are split axially along line 206 and are held together at one side by a living hinge 208 constructed of the same plastic as the disc and stem.

The circular scalpel blade 28 may thus be placed in the disc shaped recess 210 formed in the flat disc portion 202 of the blade protector structure 200 with the halves of the protector separated by bending the living hinge 208. The protector 200 is then reformed in the configuration shown in FIGS. 20 and 21 and a hollow cylinder 212 which is split at 214 axially along one side thereof is positioned over the stem 204 to hold the protector in a closed position.

The cylinder 212 is constructed of resilient plastic and the internal diameter thereof is slightly smaller than the external diameter of the stem 204 of the retainer 200.

Thus, with the structure illustrated in FIGS. 20 and 21, a circular scalpel blade may be easily transported and moved about without danger of damaging the scalpel blade periphery or cutting someone.

The modification of the circular scalpel structure 10 illustrated in FIG. 22 includes a modified circular blade support arm 220. Similarly, the modification of FIG. 23 includes a further modified blade support arm 222 as will be seen from a comparison of FIGS. 22 and 23. The support arms 22, 220 and 222, respectively, support a circular scalpel blade 28 at an angle of 45° to the axis of the circular scalpel 10, and transverse to the axis of the handle of the circular scalpel 10, respectively. Each of the circular scalpel blades is positioned on the axis of the handle of the circular scalpel 10.

The different support arms 22, 220, and 222 each provide a cleared area between the end of the handle and the scalpel blade so that the surgeon has maximum visual excess to an incision being made.

Specifically, with the support arm 22, the support arm is secured to the retaining structure 54 and extends in a circular arc for approximately 135° after which it extends straight to the intersection of the support arm and the axis of the handle of the circular scalpel 10. With the structure of FIG. 22, the support arm extends initially in a full 180° circular arc and then straight to the axis of the handle of the circular scalpel 10. The structure of FIG. 23 is slightly different in that it first extends approximately 135° in a circular arc, then extends for a short straight portion followed by a reverse curvature of 45° to the axis of the handle of the circular scalpel 10. The initial curvature and the reverse curvature are the same arcuate configuration in the structure of FIG. 23.

The manual circular scalpel 228 shown in FIG. 24 includes a handle 230 which is formed at 232 to aid the surgeon's grip thereon. Further, the handle 230 is bifurcated at end 234 to provide the opposed portions 236 and 238 between which the circular scalpel blade 28 is secured for rotation on axle 240. As shown best in FIG. 26, the handle 230 may be provided with an angular off-set 242 if desired to provide greater visual access for the surgeon.

In use of the manual scalpel structure 228, shown in FIGS. 24, 25, and 26, it will be understood that the surgeon will in the best practice draw the circular scalpel blade across the area in which the incision is desired at a rate such that the blade 28 will rotate at the circumference thereof at between 4 and 7 centimeters per second as indicated above to minimize scar tissue at the incision.

Figure 18:
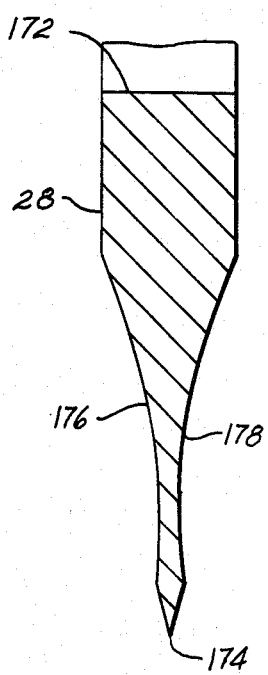
FIG. 18 is an enlarged section view of the scalpel blade illustrated in FIG. 17 taken substantially on the line 18—18 in FIG. 17.

The blade 28 will be caused to rotate due to the frictional engagement thereof with the material being cut and again the frictional engagement between the blade 28 and the material being cut will be minimized due to the concave sides 176 and 178 of the blade 28 as shown best in FIG. 18.

While different embodiments of the invention and modifications thereof have been considered in detail, it will be understood that other modifications and embodiments are contemplated by the inventor. For example, the automated rotary scalpel may be powered by a battery positioned in the handle thereof. Also, dual, transversely spaced apart rotary blades may be provided on the same scalpel to facilitate cutting of skin strips if desired. It is the intention to include all such embodiments and modifications as are defined by the appended claims within the scope of the invention.

We claim:

1. A completely manual method of making a surgical incision in free tissue comprising moving a freely rotatable circular scalpel blade across an area of the free tissue and along a line thereon where the incision is required at a desired incision depth without pressing the tissue to a mechanical backing member physically connected to the circular scalpel blade wherein the circular scalpel blade is rotated solely by friction between the blade and the tissue in which the incision is required.

2. The method of making a surgical incision as set forth in claim 1, wherein the scalpel blade is pulled across the area.

3. The method as set forth in claim 1, wherein the circular scalpel blade is moved across the tissue in which the incision is required at a speed of between 4 and 7 centimeters per second.

4. The method of making a surgical incision as set forth in claim 1, wherein the scalpel blade is pushed across the area.

5. The method as set forth in claim 4, wherein the circular scalpel blade is pushed across the tissue in which the incision is required at a speed of between four and seven centimeters per second.

6. The method as set forth in claim 1, wherein the circular scalpel blade is moved across the tissue in which the incision is required at a speed of between four and seven centimeters per second.

7. A completely manual method of making a surgical incision in free tissue comprising moving a freely rotatable circular scalpel blade across an area of the free tissue and along a line thereon where the incision is required at a desired incision depth without pressing the tissue to a mechanical backing member wherein the circular scalpel blade is rotated solely by friction between the blade and the tissue in which the incision is required.

8. A completely manual method of making a surgical incision in free tissue comprising moving a freely rotatable circular scalpel blade across an area of the free tissue and along a line thereon where the incision is required at a desired incision depth wherein the circular scalpel blade is rotated solely by friction between the blade and the tissue in which the incision is required.

* * * * *